(12) United States Patent
Dunbar et al.

(10) Patent No.: US 7,156,849 B2
(45) Date of Patent: Jan. 2, 2007

(54) ROD REDUCTION NUT AND DRIVER TOOL

(75) Inventors: William L. Dunbar, Norton, MA (US); Chris Rybicki, Fall River, MA (US); Ian Burgess, Barrington, RI (US); Ron Sacher, Needham, MA (US)

(73) Assignee: DePuy Spine, Inc., Raynham, MA (US)

( * ) Notice: Subject to any disclaimer, the term of this patent is extended or adjusted under 35 U.S.C. 154(b) by 299 days.

(21) Appl. No.: 10/462,408

(22) Filed: Jun. 16, 2003

(65) Prior Publication Data

US 2004/0254576 A1 Dec. 16, 2004

(51) Int. Cl.
*A61B 17/56* (2006.01)

(52) U.S. Cl. .................. 606/61; 81/177.85; 606/99

(58) Field of Classification Search ............. 81/177.85, 81/459, 120, 121.1, 53.2; 606/104, 73, 99
See application file for complete search history.

(56) References Cited

U.S. PATENT DOCUMENTS

| | | | |
|---|---|---|---|
| 410,780 A * | 9/1889 | Cahn | 408/206 |
| 2,800,820 A * | 7/1957 | Retterath | 81/53.2 |
| 5,020,519 A | 6/1991 | Hayes et al. | |
| 5,364,397 A | 11/1994 | Hayes | |
| 5,484,440 A | 1/1996 | Allard | |
| 5,545,165 A | 8/1996 | Biedermann et al. | |
| 5,551,320 A * | 9/1996 | Horobec et al. | 81/53.2 |
| 5,720,751 A | 2/1998 | Jackson | |
| 5,782,831 A | 7/1998 | Sherman et al. | |
| 5,910,141 A | 6/1999 | Morrison et al. | |
| 6,123,707 A | 9/2000 | Wagner | |
| 6,183,472 B1 | 2/2001 | Lutz | |
| 6,251,112 B1 | 6/2001 | Jackson | |
| 6,440,133 B1 | 8/2002 | Beale et al. | |
| 6,511,484 B1 | 1/2003 | Torode | |
| 6,648,888 B1 | 11/2003 | Shluzas | |
| 6,660,006 B1 | 12/2003 | Markworth et al. | |
| 6,726,692 B1 | 4/2004 | Bette | |
| 6,743,231 B1 | 6/2004 | Gray | |
| 6,746,449 B1 | 6/2004 | Jones | |
| 6,752,832 B1 * | 6/2004 | Neumann | 623/17.15 |
| 6,790,209 B1 | 9/2004 | Beale et al. | |
| 2001/0029376 A1 | 10/2001 | Sater et al. | |
| 2002/0095153 A1 | 7/2002 | Jones et al. | |
| 2003/0028195 A1 | 2/2003 | Bette | |
| 2003/0225408 A1 | 12/2003 | Nichols | |

FOREIGN PATENT DOCUMENTS

DE 4238339 5/1994

\* cited by examiner

*Primary Examiner*—Eduardo C. Robert
*Assistant Examiner*—James L Swiger
(74) *Attorney, Agent, or Firm*—Nutter McClennen & Fish LLP

(57) ABSTRACT

A rod reduction device is provided having a reduction nut adapted to mate to the rod-receiving portion of a spinal implant, and a driver tool that is effective to engage the reduction nut such that rotation of the driver tool rotates the reduction nut to reduce a rod positioned between the reduction nut and within the rod-receiving head of a spinal implant into the rod-seating portion of the head of the spinal implant. The driver tool can include a support 32 formed on a distal end thereof that is adapted to be disposed within the rod-receiving head of a spinal implant to prevent the rod-receiving head of the implant from collapsing during use of the rod reduction device.

24 Claims, 6 Drawing Sheets

ROD REDUCTION NUT AND DRIVER TOOL

FIELD OF THE INVENTION

The present invention relates to spinal fixation systems, and in particular to spinal rod reduction devices, spinal implants, and methods for using the same.

BACKGROUND OF THE INVENTION

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation rods can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation devices can be anchored to specific portions of the vertebra. Since each vertebrae varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped slot formed in the head. A set-screw, plug, or similar type of fastening mechanism is used to lock the fixation rod into the rod-receiving portion of the pedicle screw. In use, the shank portion of each screw is then threaded into a vertebra, and once properly positioned, a fixation rod is seated through the rod-receiving portion of each screw and the rod is locked in place by tightening a cap or similar type of locking mechanism to securely interconnect each screw and the fixation rod.

While current spinal fixation systems have proven effective, difficulties have been encountered in mounting rods into the rod-receiving portion of various fixation devices. In particular, it can be difficult to align and seat the rod into the rod receiving portion of adjacent fixation devices due to the positioning and rigidity of the vertebra into which the fixation device is mounted. Thus, the use of a spinal rod approximator or a spinal rod reducer is often required in order to grasp the head of the fixation device and reduce the rod into the rod-receiving portion of the fixation device.

While several rod approximators are known in the art, some tend to be difficult and very time-consuming to use. Accordingly, there remains a need for an improved rod approximator/reducer, implants for use with rod approximators/reducers, and methods for seating a spinal rod in a rod-receiving portion of one or more spinal implants.

SUMMARY OF THE INVENTION

The present invention generally provides a rod reduction device for reducing a rod disposed within a rod-receiving recess formed in a rod-receiving head of a spinal implant. The rod reduction device includes a reduction nut having a proximal end, a distal end, and a sidewall extending therebetween defining inner and outer surfaces. Threads are formed on the inner surface of the reduction nut adjacent to the distal end. The device further includes a driver tool having an elongate shaft with proximal and distal ends. The distal end is sized to engage the reduction nut such that rotation of the driver tool is effective to rotate the reduction nut to thread the nut onto the rod-receiving head of a spinal implant to reduce a rod disposed therein. The driver tool can also include a support member adapted to be positioned within the rod-receiving head of the spinal implant to prevent the head from collapsing inward during reduction of the rod. The support member can be, for example, a hollow cylindrical tube formed on a distal-most end of the driver tool and having an outer diameter less than an inner diameter of the reduction nut.

The reduction nut can have a variety of configurations, and in one embodiment it has a substantially cylindrical shape, and a length equal to or greater than a length of the support member. A drive surface is preferably formed on the reduction nut adjacent to the proximal end for engagement with a corresponding driver member formed on the elongate shaft of the driver tool. The drive surface can be a hexagonal socket formed on the inner surface of the reduction nut that is adapted to receive a hexagonal shaped driver member formed on the driver tool. In use, the distal end of the elongate shaft of the driver tool preferably interferingly engages the reduction nut.

In another embodiment, the reduction nut can be fixedly attached to or integrally formed with a distal end of the elongate shaft of the driver tool, and a cowl can be axially secured to, but freely rotatable around the reduction nut. The cowl preferably has a distal end that extends a predetermined distance beyond the distal end of the reduction nut such that the cowl is effective to engage and reduce a rod within the rod-receiving head of a spinal implant. In an exemplary embodiment, at least one rod-receiving recess is formed in the distal end of the cowl and is effective to seat a rod.

In yet another embodiment of the present invention, a rod reduction device is provided having an elongate member with a proximal, handle end, and a distal end including a mating element formed thereon with a support extending distally from the mating element. The device also includes a hollow, cylindrical reduction nut having a proximal end adapted to be disposed around and to mate to the mating element formed on the elongate member, and a distal end having internal threads formed therein. In use, the support is adapted to be disposed within the rod-receiving portion of a spinal implant, and the internal threads formed within the reduction nut are adapted to be disposed around and to mate with external threads formed the rod-receiving portion of the spinal implant.

In other aspects of the present invention, a spinal implant kit can be provided including a spinal implant and a reduction tool. The spinal implant includes a distal, bone-engaging portion and a proximal, U-shaped head defining first and second opposed legs. Each leg of the U-shaped head includes an irreplaceably removable extension having external threads formed thereon. The reduction tool includes a reduction nut having a proximal end, a distal end, and an inner lumen extending therebetween. Threads are formed within the inner lumen of the reduction nut adjacent the distal end for mating with the external threads formed on the extension of each leg of the U-shaped head of the spinal implant. The reduction tool further includes a driver tool having a proximal, griping end and a distal end adapted to non-rotatably engage to the reduction nut to effect rotational movement of the reduction nut. A support member is formed on the distal end of the driver tool and is adapted to be disposed between the opposed legs of the U-shaped head of the spinal implant.

Methods for using the devices of the present invention are also provided.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
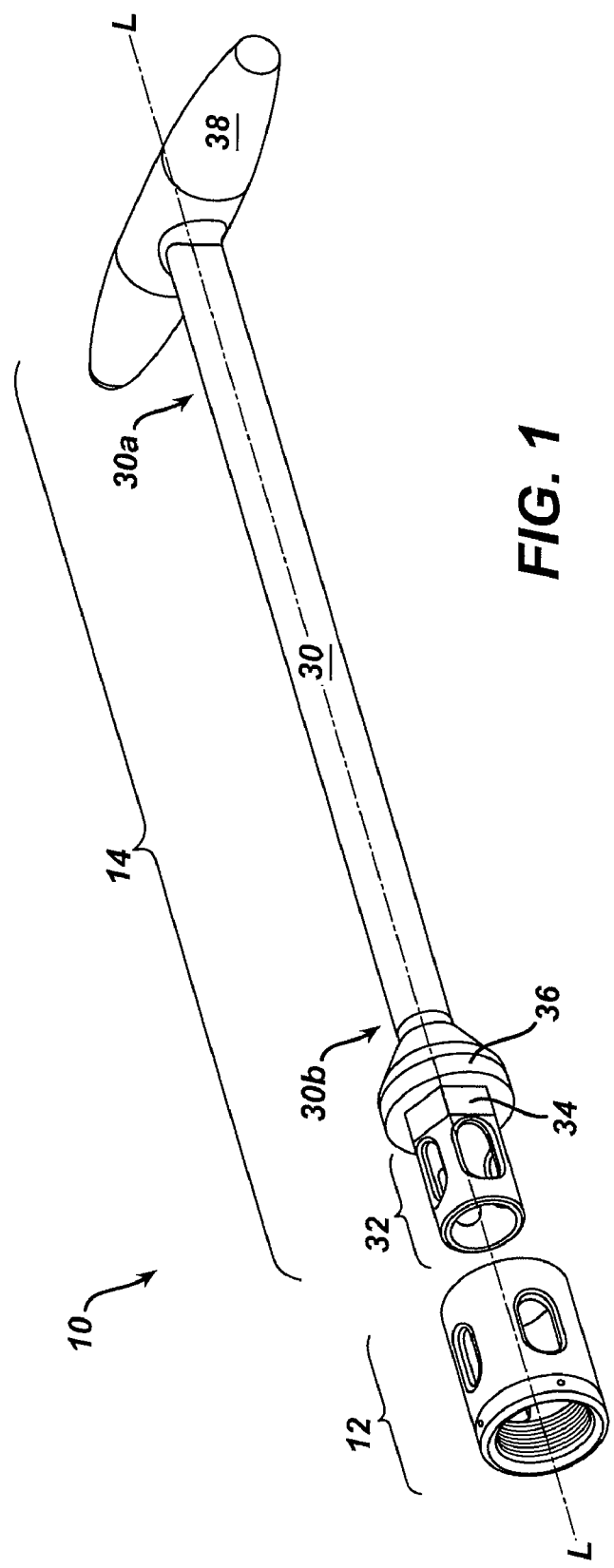
FIG. 1 is a perspective view of a rod reduction device having a driver tool and a reduction nut according to one embodiment of the present invention.

As shown in FIG. 1, the present invention generally provides a rod reduction device 10 having a reduction nut 12 adapted to mate to the rod-receiving portion of a spinal implant, and a driver tool 14 that is effective to engage the reduction nut 12 such that rotation of the driver tool 14 rotates the reduction nut 12 to reduce a rod positioned between the reduction nut 12 and within the rod-receiving head of a spinal implant into the rod-seating portion of the head of the spinal implant. The driver tool 14 can also include a support member 32 formed on a distal end 30b thereof that is adapted to be disposed within the rod-receiving head of a spinal implant to prevent the rod-receiving head of the implant from collapsing during use of the rod reduction device 10. The device 10 is particularly advantageous in that it provides a mechanical mechanism for reducing a rod, thereby allowing a closure mechanism to be easily mated to the implant to secure the rod therein. The device is also advantageous in that several reduction nuts can be used with several implants, and the driver tool can be used to reduce the rod into each implant in increments, thereby gradually decreasing the force required to reduce the rod.

Figure 2A:
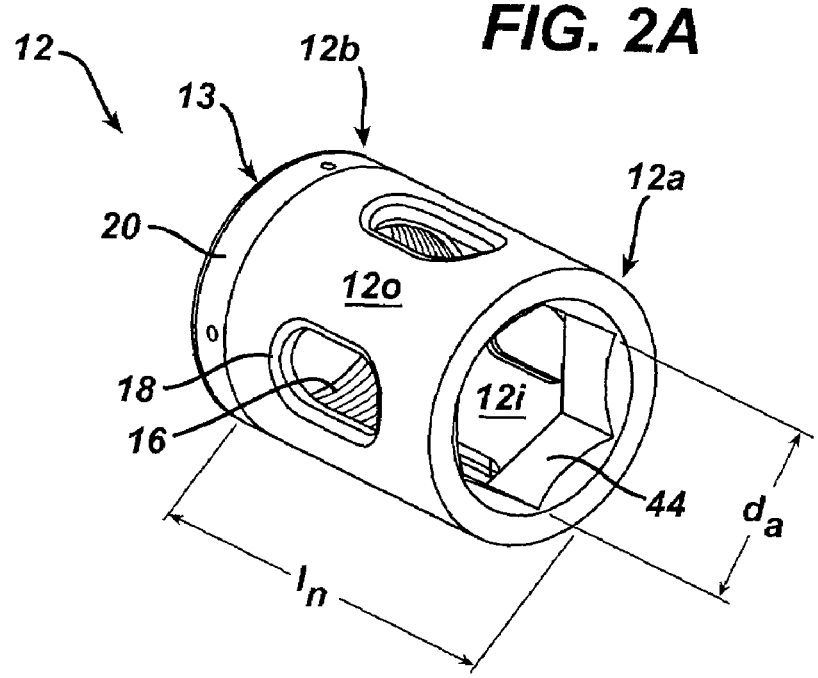
FIG. 2A is a perspective view of the reduction nut shown in FIG. 1.
Figure 2B:
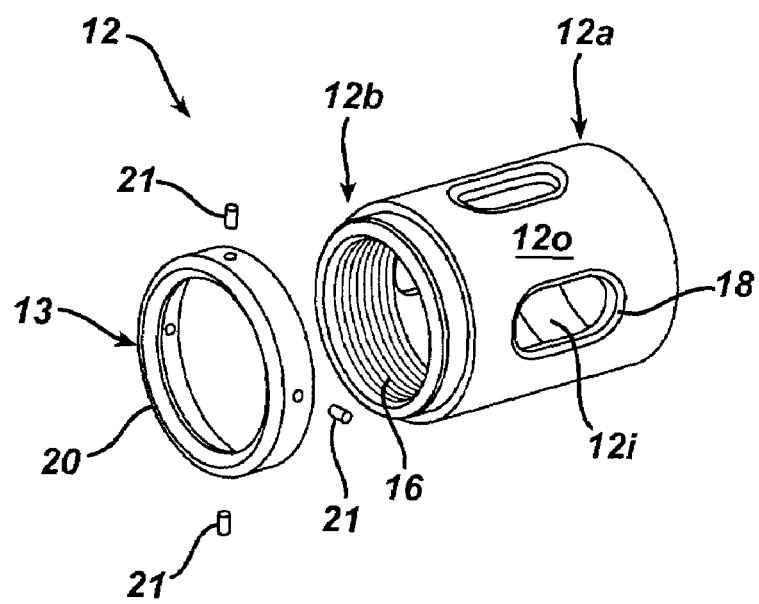
FIG. 2B is an exploded view of the reduction nut shown in FIGS. 1 and 2A.

The reduction nut 12, which is shown in more detail in FIGS. 2A and 2B, can have a variety of configurations, but in an exemplary embodiment is a substantially hollow, cylindrical member having a proximal end 12a, a distal end 12b, and a sidewall extending therebetween defining inner and outer surfaces 12i, 12o. The sidewall of the reduction nut 12 can be substantially solid, or it can include one or more openings 18 formed therein for providing visual access to the inner lumen of the reduction nut 12, and to a spinal implant being engaged by the reduction nut 12. By way of non-limiting example, in an alternative embodiment (not shown), the sidewall that forms the reduction nut 12 can be formed from several prong or leg-type members that are adapted to engage the rod-receiving head of a spinal implant.

The distal end 12b of the reduction nut 12 is adapted to receive and engage the rod-receiving head of a spinal implant, and thus can include a mating element, such as threads 16, formed on an inner surface 12i thereof. The threads 16 are adapted to mate with corresponding threads formed on at least a portion of an outer surface of the rod-receiving head of a spinal implant, which will be discussed in more detail with respect to FIGS. 5A and 5B. In use, as the reduction nut 12 is threaded onto the implant, the distal-most end 13 of the reduction nut 12 contacts and distally reduces the rod to seat the rod within the rod-seating portion of the head of the implant. In order to prevent potential damage to the rod during reduction, the distal-most end 13 of the reduction nut 12 can optionally be formed from a material that is softer than the spinal rod. In an exemplary embodiment, shown in FIGS. 2A and 2B, the distal-most end 13 of the reduction nut 12 includes a ring member 20, preferably formed from a plastic material, which contacts the spinal rod during the distally-rotational movement of the reduction nut 12 against the rod. The ring member 20 can be attached to the reduction nut 12 using pin members 21, as shown, or it can be otherwise fixedly or removably mated to the reduction nut 12 using techniques known in the art.

The proximal end 12a of the reduction nut 12 is adapted to couple to the driver tool 14, and thus can include a drive surface formed thereon. While the drive surface can have a variety of configurations, FIG. 2A illustrates an exemplary embodiment of a hexagonal socket 44 formed within the proximal end 12a of the reduction nut 12. The hexagonal socket 44 is effective to receive a corresponding hexagonal-shaped drive surface 34 (FIG. 3) formed on a distal portion of the driver tool 14, such that the driver tool 14 can engage the reduction nut 12 and rotation of the driver tool 14 is effective to rotate the reduction nut 12 to thread the nut 12 onto the rod-receiving head of a spinal implant. A person skilled in the art will appreciate that a variety of mating techniques can be used to mate the driver tool 14 to the reduction nut 12, and that the mating elements on each device 12, 14 can be formed at a variety of locations.

Figure 3:
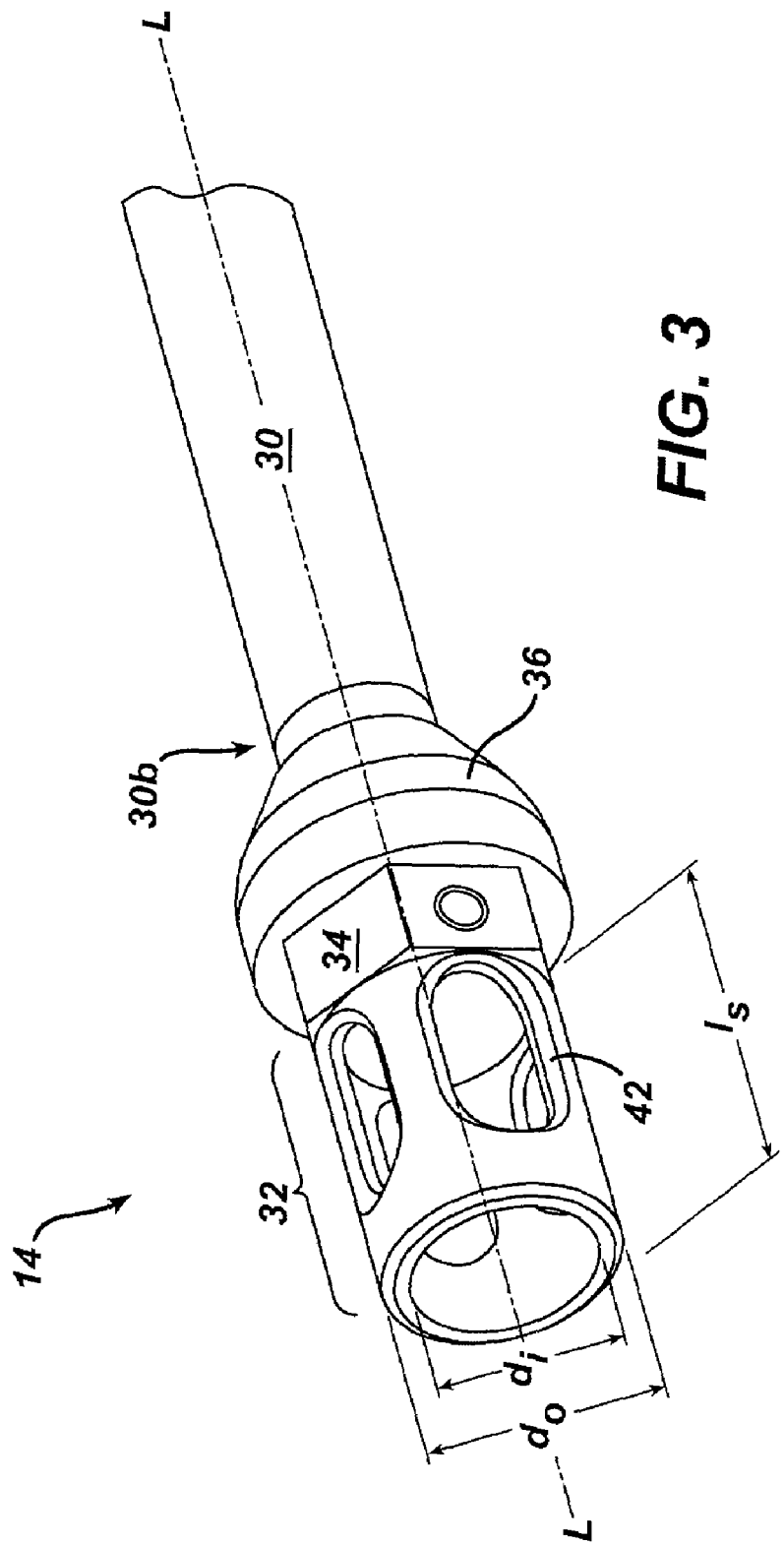
FIG. 3 is a detailed perspective view of the distal end of the driver tool shown in FIG. 1.

The driver tool 14 that is used to engage and rotate the reduction nut 12 is shown in FIGS. 1 and 3 and can also have a variety of configurations. In an exemplary embodiment, the driver tool 14 includes a shaft 30 having a proximal end 30a and a distal end 30b. The shaft 30 can have virtually any shape and size, but it is preferably generally elongate and extends along a longitudinal axis L to facilitate the proper alignment of the driver tool 14 with the reduction nut 12. The proximal end 30a of the shaft 30 can include a handle 38 formed thereon to facilitate grasping and rotation of the driver tool 14. While the handle 38 is shown as a transverse member mated to the proximal end 30a of the shaft 30, the handle 38 can have virtually any configurations, and it can be integrally formed with, fixedly attached to, or removably attached to the shaft 30.

As previously indicated, the distal end 30b of the driver tool 14 includes a drive surface 34 sized to engage the reduction nut 12 such that rotation of the driver tool 14 is effective to rotate the reduction nut 12 to thread the nut 12 onto the rod-receiving head of a spinal implant. As shown in FIGS. 1 and 3, a hexagonal surface 34 is formed around a distal portion of the driver tool 14 and is sized to securely fit within the hexagonal socket 44 in the reduction nut 12. As is further illustrated, the driver tool 14 can also include a flanged portion 36 formed around the shaft 30 just proximal to the hexagonal drive surface 34. The flanged portion 36 is adapted to abut the proximal end 12a of the reduction nut 12 to prevent over-insertion of the distal end 30b of the shaft 30 into the reduction nut 12. As previously stated with respect to the reduction nut, a person skilled in the art will appreciate that a variety of drive features can be used to engage the driver tool to the reduction nut, and that the hexagonal shaped driver is merely intended as an exemplary embodiment.

The driver tool 14 can also optionally include a support member 32 formed on the distal end 30b of the shaft, and preferably extending distally from the drive surface 34. The support member 32 should be adapted to be positioned within the rod-receiving head of a spinal implant engaged by the reduction nut to prevent the head of the spinal implant from collapsing inward as a result of the reducing force during the reduction of a spinal rod extending therethrough. Thus, the support member 32 can have a variety of configurations and it can be substantially solid, or it can include one or more openings 42 formed therein for providing visual access to the inner lumen of the support member 32 and to the inner lumen of the head of a spinal implant within which the support member 32 is disposed. In an alternative embodiment, and by way of non-limiting example, the support member 32 can include prong or leg-type members that are adapted to fit within the rod-receiving head of a spinal implant to prevent the head from collapsing during reduction of a rod disposed therein.

FIGS. 1 and 3 illustrate an exemplary embodiment of a support member 32 having a substantially hollow, cylindrical shape defining a length $l_s$ extending along the longitudinal axis L, an outer diameter $d_o$, and an inner diameter $d_i$. The length $l_s$ of the support member 32 can vary, but preferably the length $l_s$ is less than a length $l_n$ of the reduction nut 12 so as to allow the reduction nut 12, rather than the support member 32, to contact and reduce a rod disposed within the rod-receiving head of a spinal implant. The inner and outer diameters $d_i$, $d_o$ of the support member 32 can also vary, but the outer diameter $d_o$ of the support member 32 should be less than an inner diameter $d_a$ (FIG. 2A) of the reduction nut 12, and moreover it should be less than an inner diameter of the rod-receiving head of a spinal implant adapted to receive the support member 32. The outer diameter $d_o$ of the support member 32 should, however, have a size that is sufficient to allow the support member 32 to fit securely within the head of an implant such that the support member comes into contact with, and optionally provides an interference fit with, the inner surface of the head of the implant.

Figure 4A:
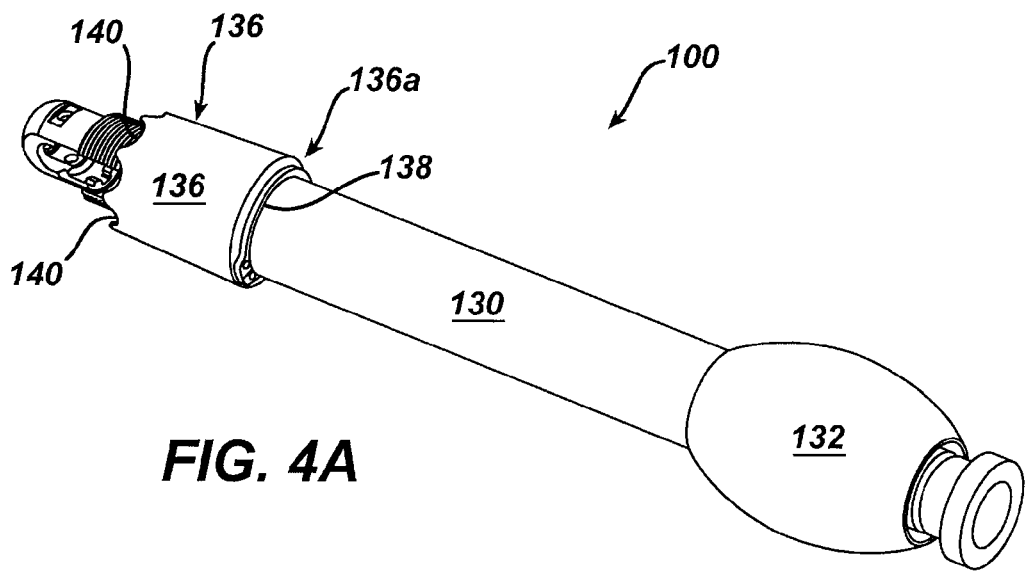
FIG. 4A is a perspective view of another embodiment of a reduction device in accordance with the present invention.
Figure 4B:
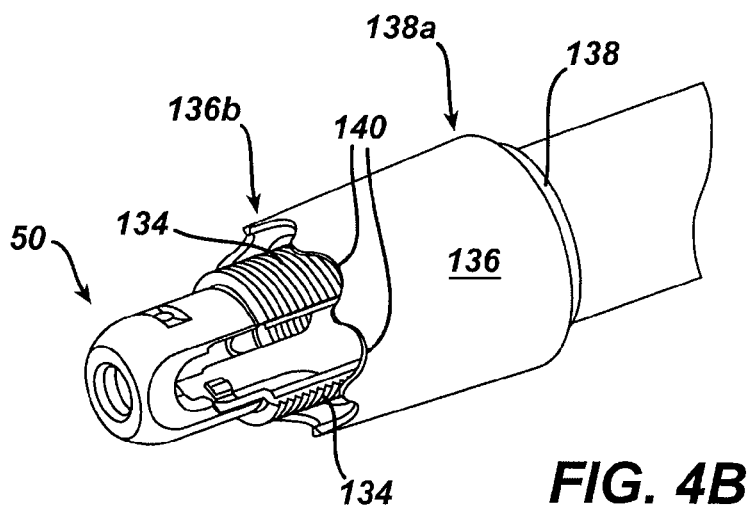
FIG. 4B is a detailed view of a distal end of the reduction device shown in FIG. 4A.

FIG. 4A illustrates another embodiment of a rod reduction device 100 that is effective for reducing a rod disposed within a rod-receiving head of a spinal implant. FIG. 4B illustrates the reduction device 100 mated a rod-receiving head 50 of a spinal screw. As shown, the reduction device 100 includes an elongate shaft 130 having a proximal, handle end 132 and a distal end 134 (partially shown in FIG. 4B) having threads (not shown) formed therein that are adapted to mate with corresponding threads 58 formed on the head 50 of a spinal implant. The reduction device 100 is similar to reduction device 10, except that the driver tool and the reduction nut are integrally formed with, or fixedly connected to, one another to form the elongate shaft 130. The reduction device 100 can also include a support member (not shown), similar to support member 32 previously described with respect to FIGS. 1 and 3. The support member is positioned within and spaced apart from the distal end 134 of the elongate shaft 130, and it is adapted to be disposed within the head 50 of the spinal implant. Since in one embodiment the distal, threaded end 134 is not removable from the elongate shaft 130, unlike reduction nut 12 of device 10, the device 100 cannot be removed from the head 50 until a closure mechanism is applied to the head 50 to hold the rod in the reduced position. Accordingly, the device 100 preferably includes an inner lumen extending through the entire length of the elongate shaft 130 to allow a medical tool to be inserted therethrough to apply a closure mechanism to the rod-receiving portion of the spinal implant to lock the spinal rod therein.

As is further illustrated in FIGS. 4A and 4B, the device 100 can also include a reduction cowl 136 that is effective to engage and reduce a rod within the rod-receiving head of a spinal implant. The reduction cowl 136 allows the shaft 130 and the support member (not shown) to rotate while the cowl 136 remains engaged to the rod to reduce the rod disposed within the rod-receiving head of the implant. This is particularly advantageous in that the reduction of the rod by the reduction cowl 136, rather than by the distal-most end of the elongate shaft 130, avoids the potential for scoring or otherwise causing damage to the rod during reduction.

The reduction cowl 136 can have a variety of configurations, but it is preferably a generally hollow, cylindrical member having an open distal end 136b that is effective to engage and reduce a rod disposed within the rod-receiving head 50 of the implant. The distal end 136b can optionally include one or more rod-receiving recesses 140 formed therein for seating the rod. The reduction cowl 136 further includes a proximal end 136a that is axially secured to, but freely rotatable around the distal, threaded portion 134 of the elongate shaft 130. A variety of techniques can be used for rotatably mating the reduction cowl 136 to the shaft 130. By way of non-limiting example, an annular ring 138 can be mated to the proximal end 136a of the cowl 136 and disposed within a corresponding groove (not shown) formed in the elongate shaft 130. The ring 138 and groove are effective to prevent axial movement of the reduction cowl 136 with respect to the shaft 130, yet to allow rotatable movement between the reduction cowl 136 and the shaft 130.

A person skilled in the art will appreciate that the device 100 can have a variety of configurations, and that distal, threaded end 134 of the shaft 130 can be removable to provide a separate reduction nut, similar to nut 12 described above with respect to FIGS. 2A and 2B.

Figure 5A:
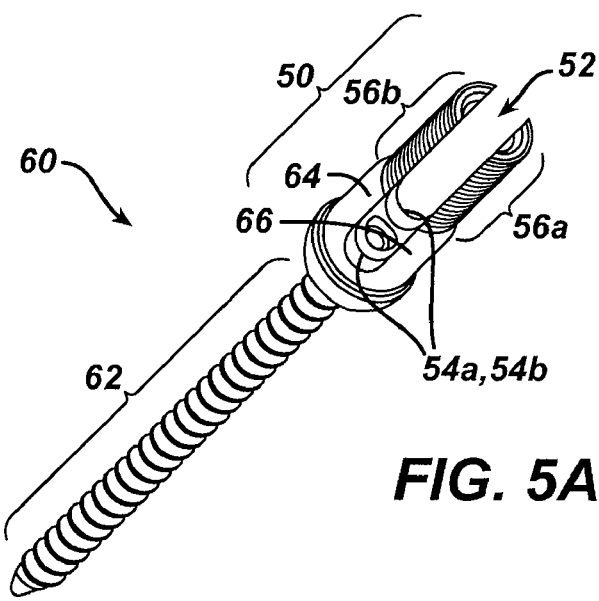
FIG. 5A is a perspective view of one embodiment of a spinal screw for use with the reduction devices of the present invention.
Figure 5B:
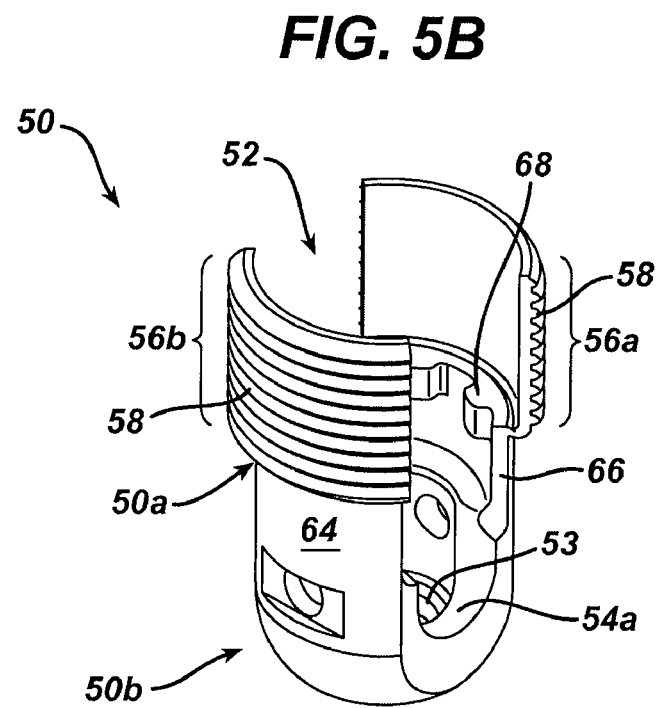
FIG. 5B is a perspective view of the rod-receiving head of the spinal screw shown in FIG. 5A.

The rod reduction devices 10, 100 of the present invention can be used with a variety of spinal implants including, for example, spinal screws, hooks, bolts, and wires. FIGS. 5A and 5B illustrate an exemplary embodiment of a spinal screw 60 that can be used with the rod reduction devices 10, 100 of the present invention. As shown, the spinal screw 60 includes a distal, bone-engaging portion, e.g., a threaded shank 62, and a proximal, U-shaped, rod-receiving head 50 that is adapted to seat a spinal rod (not shown). The threaded shank 62 can be fixedly attached to the rod-receiving head 50 to form a monoaxial screw, or alternatively the shank 62 can be configured as a polyaxial screw that is rotatably disposed through an opening 53 formed in the distal end 50b of the rod-receiving head 50 to allow rotation of the shank 62 with respect to the rod-receiving head 50. A variety of techniques can be used to allow rotation of the head 50 with respect to the shank 62. In the illustrated embodiment, the shank 62 has an enlarged proximal portion, e.g., a spherical head, that can rest within the distal end 50b of the head 50 to prevent the shank 62 from extending completely through the bore 53.

The U-shaped, rod-receiving head 50, which is shown in more detail in FIG. 5B, includes opposed side walls or legs 64, 66 that define a rod-receiving portion 52 for seating a spinal fixation rod. The legs 64, 66 are substantially parallel to one another, and include a mating element 68 formed on an inner, proximal surface thereof for mating with a closure mechanism effective to secure a rod within the rod-receiving portion 52 of the head 50. By way of non-limiting example, threads or a twist-lock mating element can be used to mate the head 50 to a closure mechanism. The rod-receiving head 50 further includes opposed rod-seating recesses 54a, 54b formed in the distal end 50b of the head 50 and extending between each of the legs 64, 66. The rod-seating recesses 54a, 54b are effective to seat a rod, which can be retained therein by an interference fit with the closure mechanism.

The rod-receiving head 50 can also include irreplaceably removable extension members 56a, 56b connected to and extending proximally from the opposed legs 64, 66. The extension members 56a, 56b each include threads 58 formed on an outer surface thereof for mating with the corresponding threads 16 formed on the inner surface of the reduction nut 12 (FIGS. 2A and 2B). The extension members 56a, 56b allow a rod, which would otherwise be positioned a distance apart from the legs of the head 50, to be reduced by the reduction nut 12 into the rod-seating recesses 54 formed in the head 50. Once the rod is reduced, the extension members 56a, 56b can be broken or snapped off of the rod-receiving head 50 and discarded. To facilitate removal, the extension members 56a, 56b can be scored at the desired break-off point, which is preferably located at the proximal-most end 50a of the rod-receiving head 50. A person skilled in the art will appreciate that the rod reduction devices 10, 100 of the present invention, while described for use in connection with a spinal implant having threaded extension members, can be adapted to mate with a variety of implants, including implants having threads formed on an inner or an outer thereof.

Figure 6:
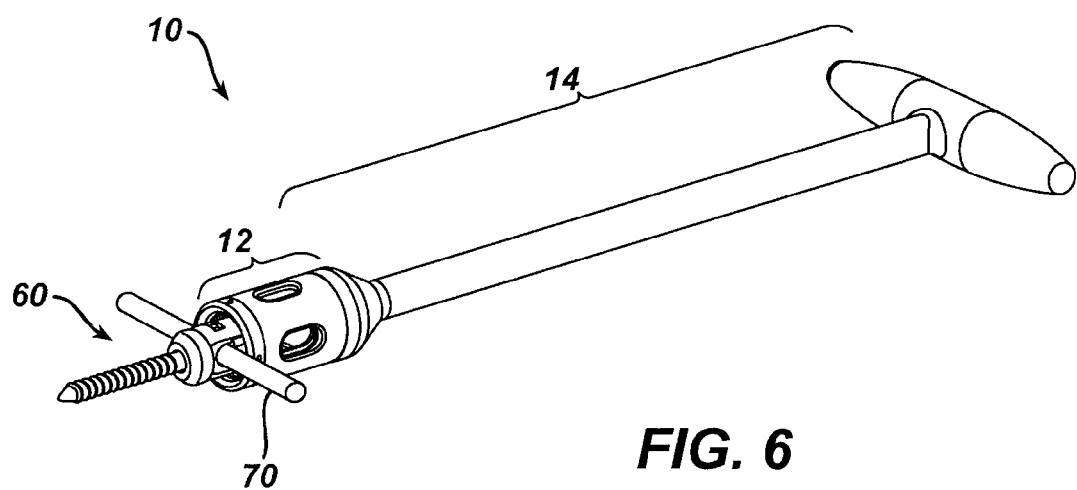
FIG. 6 is an illustration showing the rod reduction device of FIG. 1 in use with the spinal screw of FIG. 5A.

FIG. 6 illustrates device 10 in use. Prior to use of a reduction device, one or more spinal implants, e.g., spinal screw 60, are screwed into vertebral bone structures. A rod 70 is then placed within the rod-receiving head 50 of each of the implants. Typically, where two spinal implants 60 are fastened into adjacent vertebra, a spinal rod 70 is inserted into the rod-receiving head 50 of each implant 60. However, due to the alignment of the implants 60, it can be difficult to position the rod 70 within each rod-receiving portion 52. Thus, the rod reduction devices 10, 100 of the present invention can be used to mechanically force the rod into the rod-seating recesses 54. As shown, a reduction nut 12 can be loosely threaded onto the extension members 56a, 56b of the head 50 of implant 60 so that the rod 70 is positioned between the reduction nut 12 and the rod-receiving portion 52 of the implant 60. Preferably, several nuts 12 are provided as a kit and a nut 12 is threaded onto the head 50 of each implant 60. The driver device 14 can then be inserted into each reduction nut 12 such that the support member 32 is disposed between the extension members 56a, 56b, and the hexagonal drive surface 34 engages the hexagonal socket 44 on the reduction nut 12. The driver tool 14 is then rotated to further thread the reduction nut 12 onto the extension members 56a, 56b, thereby pushing the rod 70 into the rod-seating recesses 54a, 54b formed in the head 50 of the spinal implant 60. Preferably, each reduction nut 12 is threaded onto the head 50 of each implant 60 in increments to facilitate the proper alignment of the rod 70 and each implant 60. When the rod 70 is fully seated within the rod-seating recesses 54a, 54b, and the reduction nut 12 cannot be further threaded onto the extension member 56a, 56b of each implant 60, the driver tool 14 can be removed from the reduction nut 12 and a separate device can be used to apply a closure mechanism onto the head 50 of the spinal implant 60 to secure the rod 70 within the rod-receiving head 50. Each reduction nut 12 can then be removed from each implant 60, either manually or using the driver tool 14, and the extension members 56a, 56b can be broken off from the implant 60 and discarded.

Where the one piece device 100 is used, reduction can only be done on one spinal implant at a time since the reduction nut is attached to the driver tool. Thus, once reduction is complete, a tool introduced through the lumen extending through the device to apply the closure mechanism. The device can then be removed by unthreading the shaft 130 from the head 50 of the implant 60.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A rod reduction device for reducing a rod disposed within a rod-receiving recess formed in a rod-receiving head of a spinal implant, the rod reduction device comprising:
   a reduction nut having a proximal end, a distal end, and a sidewall extending therebetween defining inner and outer surfaces, the reduction nut further including threads formed on the inner surface adjacent to the distal end; and
   a driver tool including an elongate shaft having proximal and distal ends, the distal end being sized to engage the reduction nut such that rotation of the driver tool is effective to rotate the reduction nut to thread the nut onto the rod-receiving head of the spinal implant to reduce a rod disposed therein, the driver tool further including a hollow cylindrical tube formed on the distal-most end thereof and having an outer diameter less than an inner diameter of the reduction nut such that the hollow cylindrical tube is adapted to be positioned within the rod-receiving head of the spinal implant to prevent the head from collapsing inward during reduction of the rod.

2. The device of claim 1, wherein the reduction nut has a length equal to or greater than a length of the hollow cylindrical tube.

3. The device of claim 1, wherein the reduction nut has a substantially cylindrical shape.

4. The device of claim 1, wherein the reduction nut further includes a drive surface formed adjacent to the proximal end for engagement with a corresponding driver member formed on the elongate shaft of the driver tool.

5. The device of claim 4, wherein the drive surface on the reduction nut comprises a hexagonal socket formed on the inner surface of the reduction nut, and wherein the driver member formed on the driver tool has a hexagonal shape that is adapted to fit within the hexagonal socket in the reduction nut.

6. The device of claim 1, wherein the distal end of the elongate shaft of the driver tool interferingly engages the reduction nut.

7. The device of claim 1, wherein the reduction nut is fixedly attached to or integrally formed with a distal end of the elongate shaft of the driver tool.

8. The device of claim 7, further comprising a cowl axially secured to, but freely rotatable around the reduction nut, the cowl having a distal end that extends a predetermined distance beyond the distal end of the reduction nut such that the cowl is effective to engage and reduce a rod within the rod-receiving head of a spinal implant.

9. The device of claim 8, further comprising at least one rod-receiving recess formed in the distal end of the cowl and effective to seat a rod.

10. The device of claim 1, further comprising a handle formed on the proximal end of the elongate shaft of the driver tool.

11. The device of claim 1, wherein the driver tool further includes an inner lumen extending between the proximal and distal ends for receiving a tool.

12. The device of claim 1, wherein the hollow cylindrical tube includes an inner lumen formed therein defining an axis that is axially aligned with a longitudinal axis of the elongate member of the driver tool.

13. The device of claim 12, wherein the reduction nut defines an axis extending between the proximal and distal ends that is adapted to axially align with the longitudinal axis of the elongate member.

14. A rod reduction device, comprising:
an elongate member having a proximal, handle end, and a distal end including a mating element formed thereon with a hollow support extending distally from the mating element; and
a hollow, cylindrical reduction nut having a proximal end adapted to be disposed around and to mate to the mating element formed on the elongate member, and a distal end having internal threads formed therein, the reduction nut having a length equal to or greater than a length of the support member;
wherein the support is adapted to be disposed within a rod-receiving portion of a spinal implant, and the internal threads formed within the reduction nut are adapted to be disposed around and to mate with external threads formed on the rod-receiving portion of the spinal implant.

15. The device of claim 14, wherein the support comprises a hollow cylindrical member formed on a distal-most end of the elongate member and having an outer diameter that is less than an inner diameter of the reduction nut.

16. The device of claim 15, further comprising at least one opening formed in a sidewall of the support.

17. The device of claim 14, wherein the reduction nut has a substantially cylindrical shape.

18. The device of claim 17, further comprising at least one opening formed in a sidewall of the reduction nut.

19. The rod reduction device of claim 14, wherein the mating element on the reduction nut comprises a hexagonal socket formed within the proximal end, and wherein the mating element on the distal end of the elongate member comprises a hexagonal-shaped member adapted to fit within the hexagonal socket.

20. The device of claim 14, wherein the elongate member interferingly engages the reduction nut.

21. The device of claim 14, wherein the reduction nut is fixedly attached to or integrally formed with a distal end of the elongate member.

22. The device of claim 21, further comprising a cowl axially secured to, but freely rotatable around the reduction nut, the cowl having a distal end that extends a distance beyond the distal end of the reduction nut such that the cowl is effective to engage and reduce a rod within the rod-receiving head of a spinal implant.

23. The device of claim 22, further comprising at least one rod-receiving recess formed in the distal end of the cowl and effective to seat a rod.

24. The device of claim 14, wherein the elongate member includes a passage extending therethrough for receiving a tool.

* * * * *